United States Patent
Hayashi (10) Patent No.: US 11,182,874 B2
(45) Date of Patent: Nov. 23, 2021

(54) SIGNAL PROCESSING DEVICE AND SIGNAL PROCESSING METHOD

(71) Applicant: SONY CORPORATION, Tokyo (JP)

(72) Inventor: Tsuneo Hayashi, Chiba (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/518,344

(22) Filed: Jul. 22, 2019

(65) Prior Publication Data

US 2019/0340724 A1 Nov. 7, 2019

Related U.S. Application Data (63) Continuation of application No. 15/300,315, filed as application No. PCT/JP2015/054021 on Feb. 13, 2015, now Pat. No. 10,395,334.

(30) Foreign Application Priority Data

Apr. 11, 2014 (JP) .................................. 2014-082015

(51) Int. Cl.

| H04N 5/225 | (2006.01) |
| G06T 7/00 | (2017.01) |
| G06T 1/20 | (2006.01) |
| G06F 9/48 | (2006.01) |

(52) U.S. Cl.
CPC .............. *G06T 1/20* (2013.01); *G06F 9/4843* (2013.01); *A61B 2576/00* (2013.01); *G06T 2200/28* (2013.01)

(58) Field of Classification Search
CPC ........ A61B 1/00193; H04N 2005/2255; H04N 13/0203
See application file for complete search history.

(56) References Cited

U.S. PATENT DOCUMENTS

| 6,009,523 A | 12/1999 | Owaki et al. |
| 2003/0158893 A1 | 8/2003 | Komatsu et al. |
| 2006/0242618 A1 | 10/2006 | Wang et al. |
| 2007/0268296 A1* | 11/2007 | Ledebohm ............... G06T 1/20 345/501 |

(Continued)

FOREIGN PATENT DOCUMENTS

| AR | 000892 A1 | 8/1997 |
| AU | 4632496 A | 8/1996 |

(Continued)

OTHER PUBLICATIONS

Office Action for JP Patent Application No. 2016-512618, dated May 7, 2019, 07 pages of Office Action and 05 pages of English Translation.

(Continued)

*Primary Examiner* — Yi Yang
(74) *Attorney, Agent, or Firm* — Chip Law Group (57) ABSTRACT

Provided is a signal processing device including a determination unit that determines a state of software associated with image processing on an input image signal indicating an image captured by a medical apparatus, and an output control unit that has a first processed image signal that is the input image signal on which image processing has been performed by the software selectively outputted, on the basis of a result of determination of the state of the software.

15 Claims, 4 Drawing Sheets

(56) References Cited

U.S. PATENT DOCUMENTS

| | | | |
|---|---|---|---|
| 2008/0009669 A1 | 1/2008 | Ozawa et al. | |
| 2010/0318746 A1 | 12/2010 | Troxel et al. | |
| 2012/0001615 A1 | 1/2012 | Levine | |
| 2012/0288178 A1 | 11/2012 | Uebayashi et al. | |
| 2012/0288194 A1 | 11/2012 | Nakamura et al. | |
| 2013/0138892 A1* | 5/2013 | Loh | G06F 12/0893 |
| | | | 711/134 |
| 2013/0141543 A1 | 6/2013 | Choi et al. | |
| 2013/0262762 A1* | 10/2013 | Igashira | G06F 3/0656 |
| | | | 711/114 |
| 2013/0271197 A1 | 10/2013 | Sanghani et al. | |
| 2013/0278739 A1 | 10/2013 | Tanaka et al. | |
| 2013/0342668 A1 | 12/2013 | Kasumi et al. | |
| 2014/0143524 A1* | 5/2014 | Tabaru | G06F 9/3887 |
| | | | 712/221 |

FOREIGN PATENT DOCUMENTS

| | | | |
|---|---|---|---|
| BR | 9605115 A | 10/1997 | |
| CA | 2187038 A1 | 8/1996 | |
| CN | 1146814 A | 4/1997 | |
| EP | 0754999 A1 | 1/1997 | |
| EP | 02062524 A1 | 5/2009 | |
| JP | 2002-063290 A | 2/2002 | |
| JP | 2004-290329 A | 10/2004 | |
| JP | 2006-198106 A | 8/2006 | |
| JP | 2007-317191 A | 12/2007 | |
| JP | 2008-015965 A | 1/2008 | |
| JP | 2009-195621 A | 9/2009 | |
| JP | 2009-225851 A | 10/2009 | |
| JP | 2010-004979 A | 1/2010 | |
| JP | 2010-128627 A | 6/2010 | |
| JP | 2011-254381 A | 12/2011 | |
| JP | 2012-146020 A | 8/2012 | |
| JP | 2013-540259 A | 10/2013 | |
| JP | 2015-503160 A | 1/2015 | |
| KR | 10-0268693 B1 | 10/2000 | |
| MX | 9604648 A | 9/1997 | |
| WO | 96/24894 A1 | 8/1996 | |
| WO | 1996/024894 A1 | 8/1996 | |
| WO | 2012/042771 A1 | 4/2012 | |
| WO | 2013/073418 A1 | 5/2013 | |
| WO | 2013/111684 A1 | 8/2013 | |
| ZA | 9601013 B | 8/1996 | |

OTHER PUBLICATIONS

Extended European Search Report of EP Patent Application No. 15776631.2, dated Dec. 13, 2017, 08 pages.
Non-Final Office Action for U.S. Appl. No. 15/300,315, dated Nov. 17, 2017, 19 pages.
Non-Final Office Action for U.S. Appl. No. 15/300,315, dated Nov. 1, 2018, 20 pages.
Final Office Action for U.S. Appl. No. 15/300,315, dated May 23, 2018, 18 pages.
Advisory Action for U.S. Appl. No. 15/300,315, dated Aug. 3, 2018, 03 pages.
Notice of Allowance for U.S. Appl. No. 15/300,315, dated Apr. 17, 2019, 08 pages.
Notice of Allowance for U.S. Appl. No. 15/300,315, dated Apr. 29, 2019, 05 pages.
International Search Report and Written Opinion of PCT Application No. PCT/JP2015/054021, dated May 19, 2015, 10 pages of English Translation and 08 pages of ISRWO.
International Preliminary Report on Patentability of PCT Application No. PCT/JP2015/054021, dated Oct. 20, 2016, 10 pages of English Translation and 05 pages of IPRP.
Office Action for JP Patent Application No. 2019-226923 dated Dec. 8, 2020, 06 pages of Office Action and 05 pages of English Translation.

* cited by examiner

SIGNAL PROCESSING DEVICE AND SIGNAL PROCESSING METHOD

CROSS-REFERENCE PARAGRAPH

The present application is a continuation application of U.S. patent application Ser. No. 15/300,315, filed on Sep. 29, 2016, which is a National Phase patent application of International Application No. PCT/JP2015/054021 filed on Feb. 13, 2015, and which claims priority from Japanese Patent Application JP 2014-082015 filed on Apr. 11, 2014. Each of the above referenced applications is hereby incorporated by reference in its entirety.

TECHNICAL FIELD

The present disclosure relates to a signal processing device and a signal processing method.

BACKGROUND ART

There has been developed a technique of redefining the circuit configuration of a field programmable gate array (FPGA). A technique such as described in the following Patent Literature 1, for example, may be mentioned as the technique of redefining, on the basis of a result of comparison between attribute information for defining a logic circuit read from the FPGA and the expected value thereof, the circuit configuration of the FPGA by updating the attribute information.

CITATION LIST

Patent Literature

Patent Literature 1:
JP 2008-015965A

SUMMARY OF INVENTION

Technical Problem

Various devices such as those used for medical care, for example, such as an endoscope, when performing image processing on an image signal, perform image processing on an image signal by image processing hardware, for example. On the other hand, software-based image processing on an image signal is drawing attention because, for example, it is easier to change the content of image processing, and the cost required for the change is lower. However, for example, software-based image processing on an image signal has not been sufficiently used in comparison with image processing on an image signal by image processing hardware.

The present disclosure proposes a novel and improved signal processing device and a signal processing method capable of outputting an image signal on which image processing has been performed by software, when software-based image processing on an image signal is normally performed.

Solution to Problem

According to the present disclosure, there is provided a signal processing device including: a determination unit configured to determine a state of software associated with image processing on an input image signal indicating an image captured by a medical apparatus; and an output control unit configured to have a first processed image signal that is the input image signal on which image processing has been performed by the software selectively outputted, on the basis of a result of determination of the state of the software.

According to the present disclosure, there is provided a signal processing device including: a software processing unit configured to execute software associated with image processing on an input image signal that has been input; and a hardware processing unit having image processing hardware that performs image processing on the input image signal. The hardware processing unit includes a determination unit configured to determine a state of the associated software, and an output control unit configured to have a first processed image signal that is the input image signal on which image processing has been performed by the executed software selectively outputted, on the basis of a result of determination of the state of the software.

According to the present disclosure, there is provided a signal processing method including: a step of determining a state of software associated with image processing on an input image signal that has been input; and a step of having a first processed image signal that is the input image signal on which image processing has been performed by the software selectively outputted, on the basis of a result of determination of the state of the software.

Advantageous Effects of Invention

According to the present disclosure, it is possible to have an image signal on which image processing has been performed by software outputted when software-based image processing on an image signal is normally performed.

Note that the effects described above are not necessarily limited, and along with or instead of the effects, any effect that is desired to be introduced in the present specification or other effects that can be expected from the present specification may be exhibited.

DESCRIPTION OF EMBODIMENT(S)

Hereinafter, (a) preferred embodiment(s) of the present disclosure will be described in detail with reference to the appended drawings. In this specification and the drawings, elements that have substantially the same function and structure are denoted with the same reference signs, and repeated explanation is omitted.

In addition, hereinafter, description will be provided in the following order.
1. Signal processing method according to the present embodiment
2. Signal processing device according to the present embodiment (Signal Processing Method According to Present Embodiment)

Before describing the configuration of the signal processing device according to the present embodiment, the signal processing method according to the present embodiment will be first described. In the following, the signal processing method according to the present embodiment will be described, taking as an example a case where the signal processing device according to the present embodiment performs processes related to the signal processing method according to the present embodiment.

[1] Outline of the Processes Related to the Signal Processing Method According to the Present Embodiment In a case where image processing is performed on an image signal by software, it is possible to perform more advanced image processing than in a case where image processing hardware is used because, for example, it is easier to change the content of image processing, and the cost required for the change is lower.

Figure 1A:
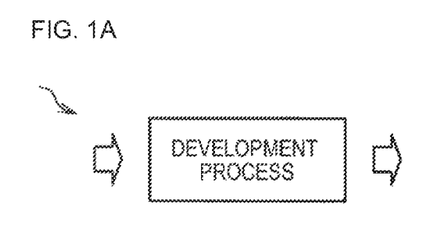
FIGS. 1A and 1B are explanatory diagrams illustrating an example of image processing in a case where image processing hardware is used and an example of image processing in a case where software is used.
Figure 1B:
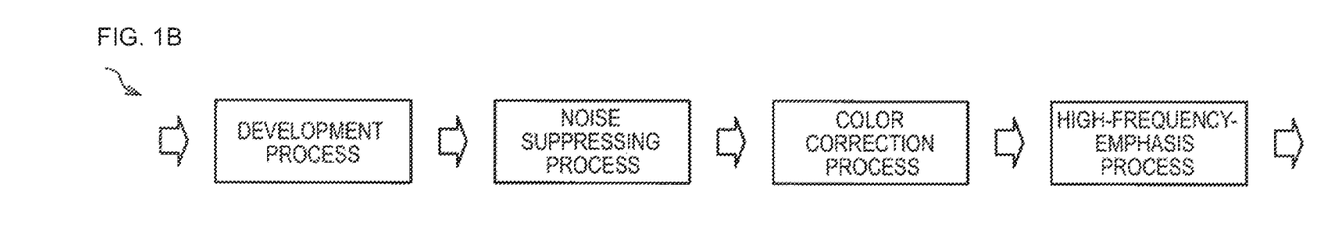

FIGS. 1A and 1B are explanatory diagrams illustrating an example of image processing in a case where image processing hardware is used and an example of image processing in a case where software is used. FIG. 1A indicates an example of image processing in the case where image processing hardware is used and FIG. 1B indicates an example of image processing in the case where software is used.

As illustrated in FIG. 1A, a development process which performs various processes relating to the development is performed on an image signal in the case where image processing hardware is used. On the other hand, in the case where software is used, as indicated by FIG. 1B, a noise suppressing process for reducing noise using a digital filter or the like, a color correction process for correcting color, and a high-frequency emphasis process for emphasizing a region having a frequency higher than a predetermined threshold value are performed on an image signal, in addition to the development process.

Here, it is also possible to implement the noise suppressing process, color correction process, high-frequency emphasis process and the like in the case where image processing hardware is used. However, it is difficult to change the content of processing in the image processing hardware that performs the development process as indicated by FIG. 1A and therefore it is very likely that new image processing hardware must be used in order to implement the noise suppressing process, color correction process, high-frequency emphasis process and the like. Accordingly, changing the content of image processing is not easy and also the cost required for the change is high in the case where image processing hardware is used. On the other hand, it is very likely that changing the content of software-based processing is easier than changing hardware.

Note that the exemplary image processing in the case where image processing hardware is used and the exemplary image processing in the case where software is used are not limited to the example illustrated in FIGS. 1A and 1B. For example, each of the image processing hardware and software may perform any image processing, or the image processing hardware and software may perform the same process.

As described above, in a case where image processing is performed on an image signal by software, it is very likely that more advanced image processing can be implemented more easily than in a case where image processing hardware is used. However, software-based image processing on an image signal has not been sufficiently used in comparison with image processing on an image signal by image processing hardware. Therefore, in the case where image processing is performed on an image signal by software, it is desired to ensure that an image signal obtained by performing image processing on an image signal by software (referred to as "first processed image signal", in the following) is an image signal obtained as a result of normal processing. In other words, it is desired to ensure as high reliability as in the case where image processing hardware is used even in the case where image processing is performed on an image signal by software.

Therefore, as a process related to the signal processing method according to the present embodiment, the signal processing device according to the present embodiment determines the state of the software associated with image processing on an image signal that has been input (referred to as "input image signal", in the following), and has a first processed image signal selectively outputted on the basis of a result of determination of the state of the software. The signal processing device according to the present embodiment has the first processed image signal outputted when the state of the software is determined to be normal, or does not have the first processed image signal outputted when the state of the software is not determined to be normal.

Here, image signals indicating a RAW image, for example, may be taken as an example of the input image signal according to the present embodiment. In addition, the input image signal according to the present embodiment may be a plurality of image signals indicating images respectively corresponding to red (R), green (G) and blue (B), for example.

In addition, image signals indicating an endoscope image captured by an imaging device included in an endoscope such as a flexible endoscope or a surgical endoscope (rigid scope), for example, may be mentioned as input image signals according to the present embodiment. Note that the input image signals according to the present embodiment are not limited to those indicating an endoscope image. For example, image signals such as those described below may be mentioned as input image signals according to the present embodiment.

Image signals indicating an image captured by an imaging device included in a surgical microscope Image signals indicating an image generated by being captured by various medical devices such as computed tomography (CT), magnetic resonance imaging (MRI), positron emission tomography (PET), ultrasonic diagnostic devices, or the like Image signals indicating an image captured by a broadcast station camera Image signals indicating an image to be displayed on a display device such as a broadcast station display device Image signals indicating an image captured by an imaging device such as a digital video camera or a digital still camera, or an imaging device included in a smart phone or the like Input image signals according to the present embodiment may be, for example, image signals generated by imaging devices such as those described above, or image signals read from a recording medium, the image signals representing image data stored in the recording medium.

In addition, image processing software which performs a variety of image processing, or system software relating to the operational environment of the image processing software such as the operating system (OS), for example, may be mentioned as software associated with image processing according to the present embodiment (may be simply referred to as "associated software", in the following). The associated software according to the present embodiment is executed by hardware such as a processor having one, or two or more processor cores, for example. A central processing unit (CPU), for example, may be mentioned as the processor according to the present embodiment. The hardware such as a processor configured to execute the associated software according to the present embodiment is, for example, hardware capable of performing processing in accordance with the software to be executed, i.e., hardware capable of performing processing generally.

In addition, the signal processing device according to the present embodiment has the first processed image signal selectively outputted by transmitting a control signal for controlling output of image signals to, for example, an output unit (described below) included in the signal processing device according to the present embodiment, or an external output device having a similar function to that of the output unit (described below).

For example, a signal (e.g., a high-level or low-level signal) which turns on or off one, or two or more switching elements included in the output unit (described below) respectively may be mentioned as the control signal according to the present embodiment. For example, a metal-oxide-semiconductor field-effect transistor (MOSFET) may be mentioned as the switching element included in the output unit (described below).

[2] Exemplary Processes Related to the Signal Processing Method According to the Present Embodiment More specifically, the signal processing device according to the present embodiment performs, for example, a determination process (1) and an output control process (2) as processes related to the signal processing method according to the present embodiment.

Note that the determination process (1) and the output control process (2) described below result from dividing the processes related to the signal processing method according to the present embodiment into two processes for convenience. Therefore, the processes related to the signal processing method according to the present embodiment may be recognized as a single process combining the determination process (1) and the output control process (2) described below, or may be recognized as two or more processes divided in an arbitrary manner. In the following, the processes related to the signal processing method according to the present embodiment will be described as being divided into the determination process (1) and the output control process (2).

(1) Determination Process

The signal processing device according to the present embodiment determines the state of the software associated with the image processing on an input image signal.

(1-1) First Example of Determination Process: Determination Based on Test Result of Hardware that Executes Associated Software The signal processing device according to the present embodiment causes, for example, the hardware that executes associated software to perform a set predetermined process. The signal processing device according to the present embodiment then determines the state of the associated software (simply referred to as "state of software", in the following), on the basis of a result of the predetermined process.

Here, a calculation process that performs a predetermined calculation may be mentioned as the predetermined process according to the present embodiment, for example. An arbitrary calculation such as "n=n+1" (n is an integer) may be mentioned as the predetermined calculation, for example.

Note that the predetermined process according to the present embodiment is not limited to a calculation process. The predetermined process according to the present embodiment may be, for example, a process of sending a response (e.g., ACK) to a response request including a response instruction. In the following, there is mainly mentioned a case where a calculation process is taken as an example for the predetermined process according to the present embodiment.

In the case where the predetermined process according to the present embodiment is a calculation process, the signal processing device according to the present embodiment determines that the state of the software is normal when the result of the calculation process is correct. In addition, in the case where the predetermined process according to the present embodiment is a calculation process, the signal processing device according to the present embodiment determines that the state of the software is not normal when the result of the calculation process is erroneous, or when the result of the calculation process is not available.

The signal processing device according to the present embodiment regularly or non-regularly transmits, to the hardware that executes the associated software, a calculation request including a calculation instruction to perform a predetermined calculation. In addition, when a calculation result for the calculation request is transmitted from the hardware that executes associated software, the signal processing device according to the present embodiment verifies the calculation result and determines the validity of the calculation result. Subsequently, in the case where the calculation result for the calculation request is correct (in the case where the calculation result is valid), the signal processing device according to the present embodiment determines that the state of the software is normal. On the other hand, in the case where the calculation result for the calculation request is not a correct result (in the case where the calculation result is not valid), or when the calculation result for the calculation request is not available, the signal processing device according to the present embodiment does not determine that the state of the software is normal.

Additionally, in a case where the predetermined process according to the present embodiment is a process of sending a response for a response request, the signal processing device according to the present embodiment regularly or non-regularly transmits a response request to the hardware that executes the associated software. Subsequently, in a case where a response is returned from the hardware that executes the associated software (or associated software that has been executed), the signal processing device according to the present embodiment determines that the state of the software is normal. In addition, the signal processing device according to the present embodiment determines that the state of the software is not normal in a case where no response has been returned from the hardware that executes the associated software (or associated software that has been executed) within a set predetermined time.

Additionally, in a case where the hardware that executes associated software has a plurality of processor cores configured to execute the associated software, the signal processing device according to the present embodiment causes some or all of the plurality of processor cores to perform a predetermined process. The signal processing device according to the present embodiment then determines the state of the software on the basis of a result of the predetermined process in the processor core which has performed the predetermined process.

Here, in a case where some of the plurality of processor cores are caused to perform the predetermined process, it is possible to reduce time and load relating to the determination process more than in a case where all of the plurality of processor cores are caused to perform the predetermined process. Alternatively, in the case where all of the plurality of processor cores are caused to perform the predetermined process, it is possible to enhance a determination precision of the state of the software more than in the case where some of the plurality of processor cores are caused to perform the predetermined process.

In a case where some or all of the plurality of processor cores are caused to perform a predetermined process, when the state of the software is determined not to be normal from the result of the predetermined process performed by the processor cores, the signal processing device according to the present embodiment can take the following measures, for example.

The first processed image signal processed by the processor core corresponding to the result of determination that the state is not normal is not outputted by the process (2) (output control process).

The processor core corresponding to the result of determination that the state is not normal is disabled and the associated software is not executed.

The first processed image signal processed by all the processor cores including the processor core corresponding to the result of determination that the state is not normal is not outputted by the process (2) (output control process).

All the processor cores including the processor core corresponding to the result of determination that the state is not normal is disabled and the associated software is not executed.

(1-2) Second Example of Determination Process: Determination Based on Authentication Result of Associated Software The signal processing device according to the present embodiment authenticates the associated software, for example, and determines the state of the software on the basis of the authentication result.

In a case where the authentication of the associated software has been normally completed, the signal processing device according to the present embodiment determines that the state of the software is normal. On the other hand, in a case where the authentication of the associated software has not been normally completed, the signal processing device according to the present embodiment determines that the state of the software is not normal.

In a case where the determination process according to the second example is performed, the associated software which has been normally authenticated is determined to be in a normal state. Therefore, it is possible to prevent the first processed image signal that has been image-processed by invalid associated software such as, for example, tampered associated software from being outputted by the signal processing device according to the present embodiment performing the determination process according to the second example.

The signal processing device according to the present embodiment authenticates the associated software by determining whether or not a response from the associated software is provided conforming to a preliminarily set authentication procedure.

As a specific example, the signal processing device according to the present embodiment transmits, to the associated software, a plain text with a set predetermined length. The associated software performs a predetermined encryption process on the transmitted plain text using a private key held by the associated software, and transmits the encrypted text resulted from encrypting the plain text to the signal processing device according to the present embodiment. The signal processing device according to the present embodiment decrypts the transmitted encrypted text and determines whether or not the decrypted plain text matches the plain text which has been transmitted to the associated software. In a case where the decrypted plain text matches the plain text which has been transmitted to the associated software, the signal processing device according to the present embodiment determines that the state of the software is normal. On the other hand, in a case where it is impossible to decrypt the transmitted encrypted text, or in a case where the decrypted plain text does not match the plain text which has been transmitted to the associated software, the signal processing device according to the present embodiment determines that the state of the software is not normal.

Note that the processing according to authentication in the determination process according to the second example is not limited to the example described above.

For example, the signal processing device according to the present embodiment can authenticate the associated software by any procedure that can authenticate the associated software.

In addition, the encryption process in the associated software may include, for example, calculation depending on a value which can be used by the signal processing device according to the present embodiment for authenticating the associated software, such as a value indicating the size of a program stored in the recording medium such as a storage unit (described below) included in the signal processing device according to the present embodiment. In a case where the calculation depending on a value which can be used by the signal processing device according to the present embodiment for authenticating the associated software is included in the encryption process in the associated software as described above, it becomes possible to further enhance the strength of tampering prevention.

(1-3) Third Example of Determination Process: Determination Based on Result of Determining Validity of First Processed Image Signal The signal processing device according to the present embodiment determines the validity of the first processed image signal, for example, and determines the state of the software on the basis of a result of determination of the validity. The signal processing device according to the present embodiment determines the validity of the first processed image signal, for example, on the basis of pixel values included in the first processed image signal.

In a case where the first processed image signal is determined to be valid, the signal processing device according to the present embodiment determines that the state of the software is normal. On the other hand, in a case where the first processed image signal is not determined to be valid, the signal processing device according to the present embodiment determines that the state of the software is not normal.

The signal processing device according to the present embodiment does not determine that the first processed image signal is valid, for example, in a case where the first processed image signal is like the following description. It goes without saying that the example of not determining that the first processed image signal according to the present embodiment is valid is not limited to the examples described below.

In a case where the first processed image signal indicates an all-black image (in a case where all the pixel values indicated by the first processed image signal are "0")

In a case where, for an input image signal indicating a video image, the difference between a first processed image signal corresponding to the preceding frame and a first processed image signal corresponding to the current frame is equal to or larger than a set threshold value (or in a case where the difference is larger than the threshold value)

In a case where, for an input image signal indicating an endoscope image, pixel values other than the masked part of the endoscope (e.g., circular part) are equal to or larger than a set threshold value (or in a case where the difference is larger than the threshold value)

In a case where the first processed image signal has an impossible pixel value

In a case where the difference between the amount of characteristic of the image indicated by the input image signal and the amount of characteristic of the image indicated by the first processed image signal is equal to or larger than a set threshold value (or in a case where the difference is larger than the threshold value)

In a case where the first processed image signal has an impossible characteristic Here, the following examples may be mentioned, for example, as specific examples of the case where the first processed image signal has an impossible pixel value.

In a case where pixel value format is 10-bit data and the image data includes 10-bit data and 6-bit invalid data, the 6-bit invalid data turns out to be non-zero data despite that the 6-bit invalid data is defined as "0".

When, in the aforementioned case, the position of the invalid data switches between the least significant bit (LSB) side and the most significant bit (MSB) side for each frame, the 6-bit invalid data turns out to be non-zero data despite that the 6-bit invalid data is defined as "0".

In addition, the example described below may be mentioned, for example, as a specific example of the case where the image indicated by the first processed image signal has an impossible characteristic.

In a case where the input image signal indicates an endoscope image, the image indicated by the first processed image signal does not have such a characteristic that "the central part is bright and the peripheral part is dark" (an example of a predetermined characteristic).

(1-4) Fourth Example of Determination Process

The signal processing device according to the present embodiment may determine the state of the software by performing each of two or more processes from the determination process according to the first example described in the aforementioned (1-1) to the determination process according to the third example described in the aforementioned (1-3).

The signal processing device according to the present embodiment determines the state of the software associated with the image processing on an input image signal by performing, as a determination process, any of the processes from the determination process according to the first example described in the aforementioned (1-1) to the determination process according to the fourth example described in the aforementioned (1-4), for example.

(2) Output Control Process

The signal processing device according to the present embodiment selectively outputs the first processed image signal, on the basis of a result of determination of the state of the software in the process (determination process) of the aforementioned section (1).

In a case where the result of determination of the state of the software in the process (determination process) of the aforementioned (1) indicates that the state is normal, the signal processing device according to the present embodiment outputs the first processed image signal. On the other hand, in a case where the result of determination of the state of the software in the process (determination process) of the aforementioned (1) indicates that the state is not normal, the signal processing device according to the present embodiment does not output the first processed image signal.

In addition, there may also be a case where image processing is performed on an input image to be processed, for example, by image processing hardware (image processing hardware included in a second image processing unit described below) included in the signal processing device according to the present embodiment, or external image processing hardware capable of communicating with the signal processing device according to the present embodiment. When, in the aforementioned case, the first processed image signal is not to be outputted, the signal processing device according to the present embodiment may output an image signal (referred to as "second processed image signal", in the following) obtained by performing image processing on an input image signal using the image processing hardware.

In a case where the image processing hardware always performs image processing on an input image to be processed, the signal processing device according to the present embodiment switches the image signal to be outputted from an output unit (described below) or the like to either the first processed image signal or the second processed image signal by transmitting, to the output unit (described below), the control signal in accordance with the result of determination of the state of the software in the process (determination process) of the aforementioned (1). In other words, the control signal according to the present embodiment serves as a switching signal for switching image signals outputted from the output unit (described below) or the like.

In a case where the result of determination of the state of the software indicates that the state is normal, for example, the signal processing device according to the present embodiment transmits, to the output unit (described below) or the like, a first control signal for outputting the first processed image signal without outputting the second processed image signal. On the other hand, in a case where the result of determination of the state of the software does not indicate that the state is normal, the signal processing device according to the present embodiment transmits, to the output unit (described below) or the like, a second control signal for outputting the second processed image signal without outputting the first processed image signal. Turning on or off one, or two or more switching elements included in the output unit (described below) or the like by the first control signal or the second control signal described above turns the image signal outputted from the output unit (described below) or the like into the first processed image signal or the second processed image signal.

Note that the image processing hardware may not always perform image processing on an input image to be processed. In a case where image processing on an input image to be processed is not always performed by the image processing hardware, the signal processing device according to the present embodiment causes the image processing hardware to perform image processing on an input image signal in a case where the state of the software is determined to be not normal in the process (determination process) of the aforementioned (1). The signal processing device according to the present embodiment causes the image processing hardware to selectively perform image processing on an input image signal by transmitting, for example, to a switching element for selectively inputting an input image signal to the image processing hardware, a signal for controlling the on- or off-state of the switching element.

In the case where the state of the software is determined to be not normal, it is possible, for example, to reduce power consumption consumed by the image processing hardware, by the signal processing device according to the present embodiment causing the image processing hardware to perform image processing on an input image signal.

The signal processing device according to the present embodiment performs, for example, the process (determination process) of the aforementioned (1) and the process (output control process) of the aforementioned (2) as processes related to the signal processing method according to the present embodiment. The signal processing device according to the present embodiment determines the state of associated software in the process (determination process) of the aforementioned (1). Subsequently, in a case where the state of the software is determined to be normal in the process (output control process) of the aforementioned (2), the signal processing device according to the present embodiment outputs the first processed image signal (image signal on which image processing has been performed by software). On the other hand, in a case where the state of the software is not determined to be normal in the process (output control process) of the aforementioned (2), the signal processing device according to the present embodiment does not output the first processed image signal.

Accordingly, the signal processing device according to the present embodiment can output the image signal on which image processing has been performed by software in a case where the software-based image processing on an image signal is normally performed.

In addition, it is possible to output the image signal on which image processing has been performed by software in a case where the software-based image processing on an image signal is normally performed, and therefore it becomes possible to ensure as high reliability as in a case where image processing hardware is used (reliability comparable to that when image processing hardware is used), for example.

(Signal Processing Device According to Present Embodiment)

Next, an exemplary configuration of the signal processing device according to the present embodiment capable of performing processes related to the above-described signal processing method according to the present embodiment will be described. The following description takes, as an example, an exemplary configuration of the signal processing device according to the present embodiment in a case where processes related to the signal processing method according to the present embodiment can be divided into the process (determination process) of the aforementioned (1) and the process (output control process) of the aforementioned (2).

Figure 2:
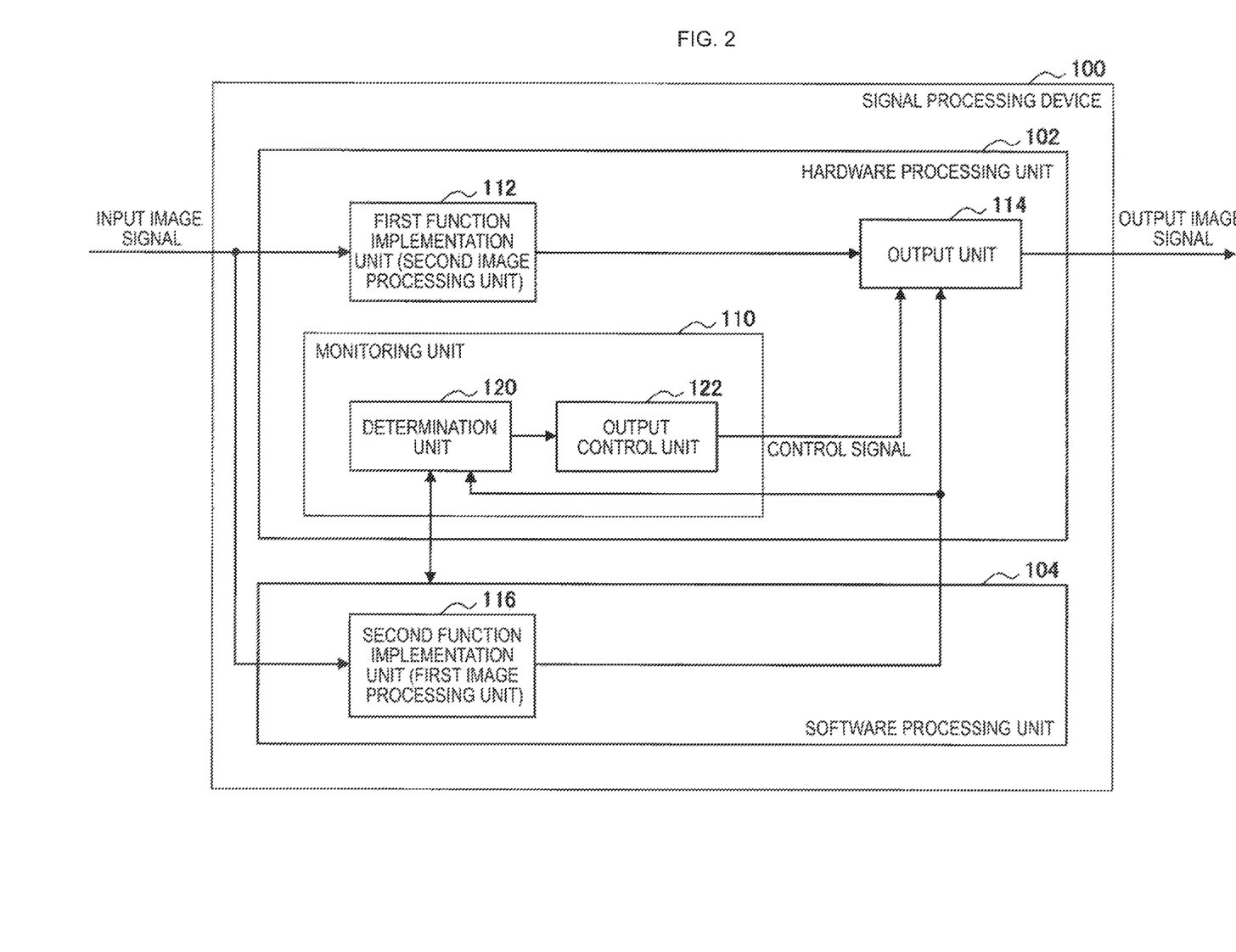
FIG. 2 is a block diagram illustrating an exemplary configuration of a signal processing device according to the present embodiment.

FIG. 2 is a block diagram illustrating an exemplary configuration of a signal processing device 100 according to the present embodiment. The signal processing device 100 includes a hardware processing unit 102 and a software processing unit 104, for example.

In addition, the signal processing device 100 may include, for example, a control unit (not illustrated), a read only memory (ROM, not illustrated), a random access memory (RAM, not illustrated), a storage unit (not illustrated), an operation unit (not illustrated) which can be operated by a user, a display unit (not illustrated) that displays a variety of screens on a display screen, and the like. The signal processing device 100 connects the respective components with each other via a bus serving as a data path, for example.

The control unit (not illustrated), including a processor constituted by a calculation circuit such as a CPU, and various processing circuits, for example, serves to control the entire signal processing device 100. In addition, the software processing unit 104, for example, may serve as the control unit (not illustrated) in the signal processing device 100.

The ROM (not illustrated) stores programs and control data such as calculation parameters to be used by the control unit (not illustrated). The RAM (not illustrated) temporarily stores programs and the like to be executed by the control unit (not illustrated).

The storage unit (not illustrated), which is storage means included in the signal processing device 100, stores a variety of data such as image data or various applications, for example. Here, a magnetic recording medium such as a Solid State Drive or a Hard Disk, a nonvolatile memory such as a flash memory, for example, may be mentioned as the storage unit (not illustrated). In addition, the storage unit (not illustrated) may be detachable from the signal processing device 100.

An operation input device such as a button, a direction key, a rotatable selector such as a jog dial, or a combination thereof, for example, may be mentioned as the operation unit (not illustrated). In addition, a display device such as Liquid Crystal Display and an Organic Electro-Luminescence Display (also referred to as Organic Light Emitting Diode Display (OLED display)) may be mentioned as the display unit (not illustrated).

[Exemplary Hardware Configuration of Signal Processing Device 100]

Figure 3:
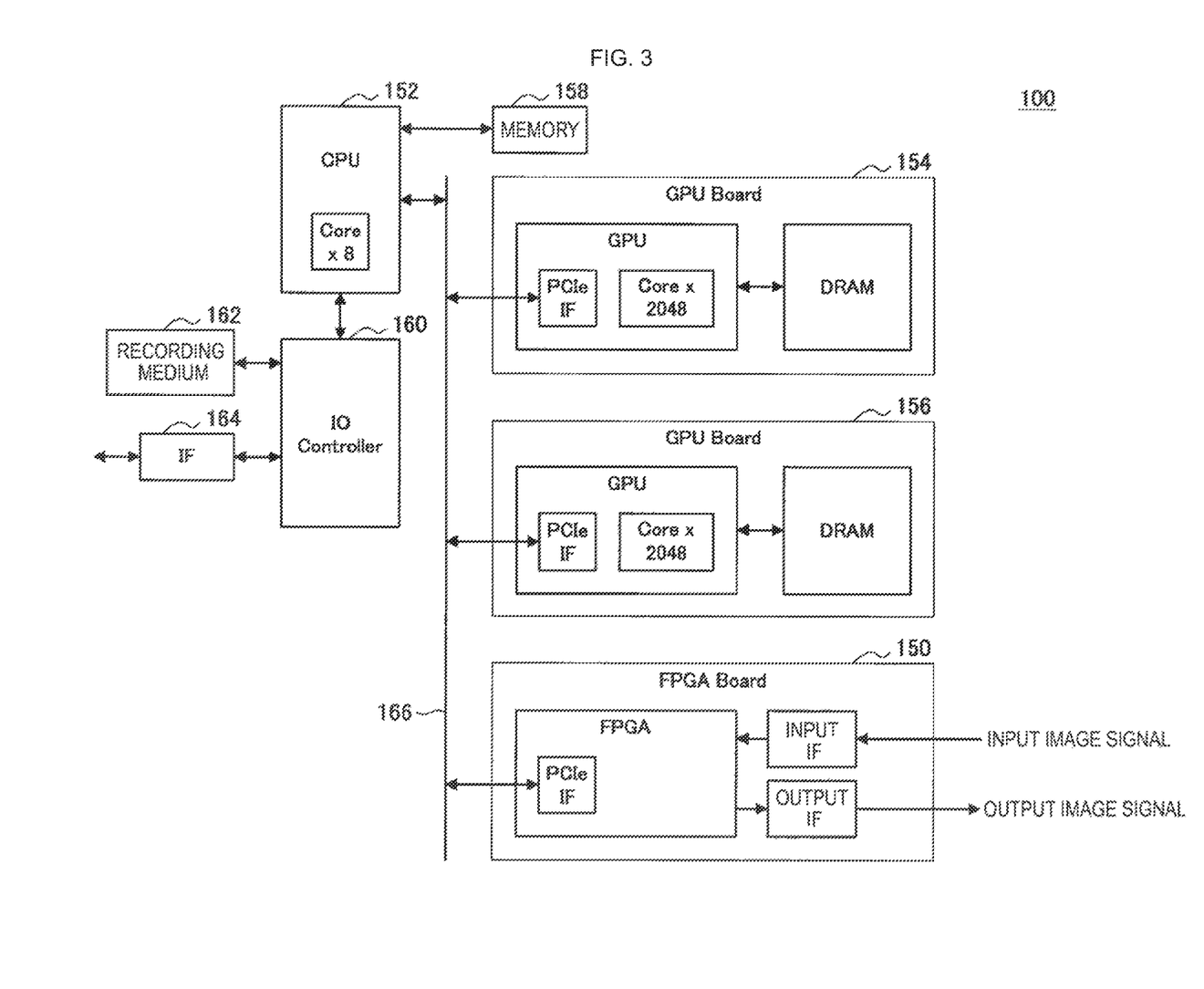
FIG. 3 is an explanatory diagram illustrating an exemplary hardware configuration of a signal processing device according to the present embodiment.

FIG. 3 is an explanatory diagram illustrating an exemplary hardware configuration of the signal processing device 100 according to the present embodiment. The signal processing device 100 includes, for example, an FPGA board 150, a CPU 152, GPU boards 154 and 156, a memory 158, an IO controller 160, a recording medium 162, and an interface 164. In addition, the FPGA board 150, the CPU 152, and the GPU boards 154 and 156 are connected by a bus 166, for example.

The FPGA board 150, which corresponds to the hardware processing unit 102 illustrated in FIG. 2, takes the initiative to perform the processes related to the signal processing method according to the present embodiment. The FPGA board 150 includes, for example, an FPGA, an input interface to which an input image signal is input, and an output interface to which the first processed image signal or the second processed image signal (may be collectively referred to as "output image signal", in the following) is outputted. In the FPGA board 150, for example, the FPGA corresponds to the hardware processing unit 102.

The CPU 152 and the GPU boards 154 and 156 correspond to the software processing unit 104 illustrated in FIG. 2. The CPU 152 and the GPU boards 154 and 156 execute a variety of software such as the associated software, for example, to perform various processes. FIG. 3 illustrates an example in which the CPU 152 includes eight core processors. In addition, the GPU boards 154 and 156 each include a graphics processing unit (GPU) and a dynamic random access memory (DRAM). FIG. 3 illustrates an example in which the GPU boards 154 and 156 each include 2048 core processors.

The memory 158 stores a variety of data such as, for example, data corresponding to an input image signal, and data corresponding to the second processed image signal. A dual inline memory module (DIMM), for example, may be mentioned as the memory 158. The CPU 152 serves to control writing and reading a variety of data to and from the memory 158.

The IO controller 160 serves to control transmission of signals among the CPU 152, the recording medium 162, and the interface 164, for example.

The recording medium 162, which functions as a storage unit (not illustrated), stores a variety of data such as image data and various applications. Here, a solid state drive or the like, for example, may be mentioned as the recording medium 162. In addition, the recording medium 162 may be detachable from the signal processing device 100.

A universal serial bus (USB) terminal and a processing circuit, and a local area network (LAN) terminal and a transmission and reception circuit, for example, may be mentioned as the interface 164.

The signal processing device 100 performs the processes related to the signal processing method according to the present embodiment with the configuration illustrated in FIG. 3, for example. Note that the hardware configuration of the signal processing device 100 according to the present embodiment is not limited to the configuration illustrated in FIG. 3.

For example, although FIG. 3 illustrates a configuration including the GPU boards 154 and 156, the signal processing device 100 according to the present embodiment need not include the GPU boards 154 and 156 in a case where the CPU 152 has the function of a GPU.

In addition, the signal processing device 100 according to the present embodiment may have any hardware configuration capable of performing the processes related to the signal processing method according to the present embodiment.

In the following, an exemplary configuration of the signal processing device 100 according to the present embodiment will be described, referring to the hardware configuration illustrated in FIG. 3 as appropriate.

Referring again to FIG. 2, an exemplary configuration of the signal processing device 100 will be described. The hardware processing unit 102 performs, by hardware, various processes such as the processes related to the signal processing method according to the present embodiment.

The hardware processing unit 102 includes, for example, a monitoring unit 110, a first function implementation unit 112 (second image processing unit), and an output unit 114. The FPGA board 150 illustrated in FIG. 3, for example, may be mentioned as the hardware processing unit 102.

The monitoring unit 110, which has a determination unit 120 and an output control unit 122, for example, takes the initiative to perform the processes related to the signal processing method according to the present embodiment.

The determination unit 120, which takes the initiative to perform the process (determination process) of the aforementioned (1), determines the state of the associated software. The determination unit 120 determines the state of associated software to be executed in the software processing unit 104.

The determination unit 120 determines the state of the associated software to be executed in the software processing unit 104 by performing, for example, any of the processes from the determination process according to the first example described in the aforementioned (1-1) to the determination process according to the fourth example described in the aforementioned (1-4).

Here, exemplary processing in the determination unit 120 will be described, taking as an example a case where the signal processing device 100 has the hardware configuration illustrated in FIG. 3.

(a) Case of Performing Determination Process According to First Example

The FPGA of the FPGA board 150 regularly (e.g., about every 16 [msec]) transmits a calculation request to software such as the OS running on the CPU 152, for example. The software running on the CPU 152 returns a calculation result such as, for example, an incremented value to the calculation request. The FPGA of the FPGA board 150 which has obtained the calculation result confirms whether or not the calculation result matches an expected value thereof. Confirming that the calculation result matches the expected value ensures, for example, that software such as the OS running on the CPU 152 has not hung up, or the software always returns a response to a calculation request (responding without exception).

Here, the CPU 152 illustrated in FIG. 3 has eight core processors operating in parallel, and the software such as the OS running on the CPU 152 allocates eight calculations to respective core processors to obtain eight calculation results. The CPU 152 then transmits the eight calculation results to the FPGA of the FPGA board 150. Note that the CPU 152 may confirm whether or not the eight calculation results match expected values thereof, and transmit the confirmation result of operation of the eight core processors to the FPGA of the FPGA board 150.

In addition, in a case where a calculation request is transmitted, the software such as the OS running on the CPU 152 transmits, to the GPUs included in the GPU boards 154 and 156, a calculation instruction to perform the calculation process indicated by the transmitted calculation request, for example. The GPUs illustrated in FIG. 3 each have 2048 core processors operating in parallel, and the software running on the CPU 152 causes the GPU to perform 2048 calculations, for example. Each of the GPUs included in the GPU boards 154 and 156 allocates 2048 calculations to respective core processors, and transmits 2048 calculation results to the CPU 152. The software running on the CPU 152 confirms, for example, whether or not the 2048 calculation results match expected values thereof, and transmits the confirmation result of the operation by the GPU to the FPGA of the FPGA board 150. Note that the software running on the CPU 152 may transmit the calculation result by the GPU to the FPGA of the FPGA board 150, for example, and the FPGA may confirm whether or not 2048 calculation results match expected values thereof.

In a case where the signal processing device 100 has the hardware configuration illustrated in FIG. 3, performing, for example, the aforementioned process in the signal processing device 100 allows the FPGA of the FPGA board 150 functioning as the monitoring unit 110 to confirm that the eight core processors of the CPU 152 and the 2048 core processors of each of the GPUs included in the GPU boards 154 and 156 are correctly responding.

Note that the example of the case where the determination process according to the first example is performed is not limited to the example described above.

For example, the core processors of each of the GPUs included in the GPU boards 154 and 156 may include integer adders, integer multipliers, floating point adders, floating point multipliers, calculators of floating point special functions (such as trigonometric function, exponential function, and logarithmic function), texture buffers, or the like. The calculation request according to the present embodiment may include a calculation instruction to test whether or not a part or all of the aforementioned calculation resources are functioning. Testing the aforementioned calculation resources allows for further enhancing the precision of determining the state of the software in the determination process according to the first example.

In addition, in a case of testing the aforementioned calculation resources, each of the regularly (e.g., such as every 16 [msec]) transmitted calculation requests may include a calculation instruction corresponding to a part of the tests of calculation resources, instead of a calculation instruction corresponding to all the tests of calculation resources. In a case where each of the regularly transmitted calculation requests includes a calculation instruction corresponding to a part of the tests of calculation resources, it is possible to further enhance the precision of determining the state of the software in the determination process according to the first example, while reducing the load of the GPUs or the like included in the GPU boards 154 and 156.

(b) Case of Performing Determination Process According to Second Example

The FPGA of the FPGA board 150 regularly (e.g., such as every 3 [msec]) authenticates software running on the CPU 152, for example.

For example, the FPGA of the FPGA board 150 transmits a plain text with a set predetermined length to the software running on the CPU 152. The software running on the CPU 152 performs a predetermined encryption process using a private key held therein, and transmits to the FPGA of the FPGA board 150 an encrypted text obtained by encrypting the plain text. The FPGA of the FPGA board 150 decrypts the transmitted encrypted text, and confirms that the decrypted plain text returns to the plain text transmitted to the software running on the CPU 152. Here, the strength of tampering prevention can be further enhanced in a case where the procedure of encryption by the software running on the CPU 152 includes a calculation depending on the size of the program stored in the recording medium 162, for example.

(c) Case of Performing Determination Process According to Third Example

The FPGA of the FPGA board 150 determines the validity of the transmitted first processed image signal, in a case where the first processed image signal is transmitted from the CPU 152 and the GPU boards 154 and 156 functioning as the software processing unit 104.

The determination unit 120 performs, for example, any of the processes from the process described in the aforementioned (a) to the process described in the aforementioned (c), or two or more processes from the process described in the aforementioned (a) to the process described in the aforementioned (c). It goes without saying that the process in the determination unit 120 is not limited to the examples described above.

The output control unit 122 takes the initiative to perform the process (output control process) of the aforementioned (2). The output control unit 122 has the first processed image signal selectively outputted, on the basis of a result of determination of the state of the software in the determination unit 120.

The output control unit 122 causes the output unit 114 to selectively output the first processed image signal by transmitting, to the output unit 114, a control signal in accordance with the result of determination of the state of the software, for example. In addition, in a case where the state of the software is determined to be not normal in the determination unit 120, the output control unit 122 causes the output unit 114, for example, to output an image signal (corresponding to the second processed image signal) obtained by processing the input image signal in the first function implementation unit 112 described below.

In addition, the output control unit 122 can also control the execution of the processing in the first function implementation unit 112 described below, on the basis of a result of determination of the state of the software in the determination unit 120, for example. The output control unit 122 causes the first function implementation unit 112 to perform processing in a case where the state of the software is determined to be not normal in the determination unit 120, for example.

The monitoring unit 110 has the determination unit 120 and the output control unit 122, for example, so as to take the initiative to perform the processes related to the signal processing method according to the present embodiment.

The first function implementation unit 112, which has image processing hardware, performs image processing on an input image signal by the image processing hardware. Although the process indicated by FIG. 1A, for example, may be mentioned as image processing in the first function implementation unit 112, image processing in the first function implementation unit 112 is not limited to the example indicated by FIG. 1A.

The first function implementation unit 112 then transmits the image signal (second processed image signal) on which image processing has been performed to the output unit 114.

The output unit 114 selectively outputs the first processed image signal transmitted from the software processing unit 104 described below, on the basis of the control signal transmitted from the output control unit 122. In addition, the output unit 114 outputs the second processed image signal transmitted from the first function implementation unit 112 in a case where the first processed image signal is not to be outputted, for example. In other words, the output unit 114 outputs the first processed image signal or the second processed image signal as an output image signal, on the basis of the control signal transmitted from the output control unit 122.

For example, a switching circuit with any configuration capable of outputting the first processed image signal or the second processed image signal on the basis of the control signal transmitted from the output control unit 122 may be mentioned as the output unit 114.

The hardware processing unit 102 includes, for example, the monitoring unit 110, the first function implementation unit 112 (second image processing unit), and the output unit 114 so as to perform various processes such as the processes related to the signal processing method according to the present embodiment.

The software processing unit 104 executes the associated software. For example, the CPU 152 and the GPU boards 154 and 156 illustrated in FIG. 3 may be mentioned as the software processing unit 104, and in the software processing unit 104, the associated software is executed by the CPU 152 or the like so as to perform various processes.

For example, the software processing unit 104, which has the second function implementation unit 116 (first image processing unit), performs image processing on an input image signal by executing the software. Although the process indicated by FIG. 1B, for example, may be mentioned as the image processing in the second function implementation unit 116, image processing in the second function implementation unit 116 is not limited to the example indicated by FIG. 1B. The input image signal processed by the second function implementation unit 116 corresponds to the first processed image signal.

Subsequently, the second function implementation unit 116 transmits the image signal (first processed image signal) on which image processing has been performed to the output unit 114.

The signal processing device 100 includes, as illustrated in FIG. 2, for example, the hardware processing unit 102 that performs the processes related to the signal processing method according to the present embodiment, and the software processing unit 104 that image-processes an input image signal by executing software.

Figure 4:
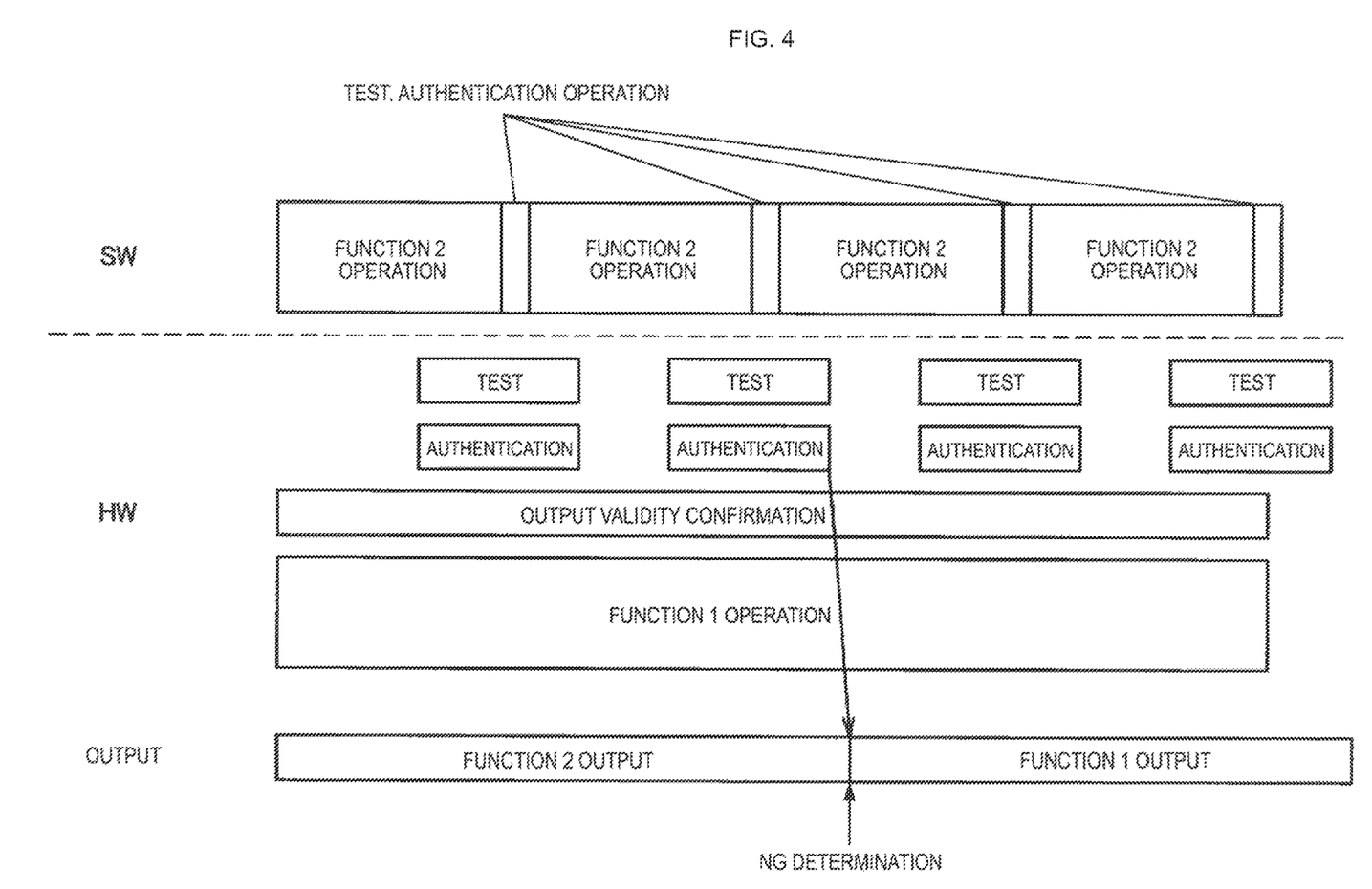
FIG. 4 is a timing chart illustrating exemplary processes performed by a signal processing device according to the present embodiment illustrated in FIG. 3.

Here, exemplary processes performed by the signal processing device 100 will be described. FIG. 4 is a timing chart illustrating exemplary processes performed by the signal processing device 100 according to the present embodiment illustrated in FIG. 3. In FIG. 4, processes in the software processing unit 104 are denoted as "SW" and processes in the hardware processing unit 102 are denoted as "HW". Additionally, in FIG. 4, the first function implementation unit 112 of the hardware processing unit 102 is denoted as "function 1" and the second function implementation unit 116 of the software processing unit 104 is denoted as "function 2".

Taking as an example a case where the input image signal is an image signal indicating a video image, the hardware processing unit 102 (more precisely, the monitoring unit 110) and the software processing unit 104 in the signal processing device 100 communicate with each other for every one frame (1/60 [sec]), for example.

The determination unit 120 of the hardware processing unit 102 performs, for every one frame, the determination process (determination based on test result) according to the first example described in the aforementioned (1-1) and the determination process (determination based on authentication result) according to the second example described in the aforementioned (1-2), for example. In addition, the determination unit 120 of the hardware processing unit 102 performs, for example, the determination process (determination based on result of determination of validity of first processed image signal) according to the third example described in the aforementioned (1-3) successively each time the first processed image signal is obtained from the software processing unit 104.

In a case where the result of determination of the state of the software indicates that the state is not normal ("NG determination" illustrated in FIG. 4) in the determination unit 120 of the hardware processing unit 102, the output image signal is switched from the first processed image signal ("function 2 output" illustrated in FIG. 4) to the second processed image signal ("function 1 output" illustrated in FIG. 4) from the frame next to the frame for which the result of determination of the state of the software indicates that the state is not normal.

In a case where the output image signal is switched from the first processed image signal to the second processed image signal, the signal processing device 100 may perform the following operations, for example.

Prompt the user to perform reactivation because the operation of the software processing unit 104 has been incomplete (a visual prompt using characters, images, light, etc., or an audio prompt using sound (including music), etc.).

Switch the output image signal from the second processed image signal ("function 1 output" illustrated in FIG. 4) to the first processed image signal ("function 2 output" illustrated in FIG. 4) in a case where the result of determination of the state of the software indicates that the state is normal.

Prompt a user to contact a preset contact destination (e.g., software maker, or maker of the signal processing device 100, etc.) because there is a possibility of tampering of software in a case where the result of determination of the state of the software by the determination process (determination based on authentication result) according to the second example described in the aforementioned (1-2) indicates that the state is not normal.

Transmit information (data) indicating the possibility of tampering of software to a preset transmission destination (e.g., an external device such as a server of the software maker, or the server of the maker of the signal processing device 100) in a case where the result of determination of the state of the software by the determination process (determination based on authentication result) according to the second example described in the aforementioned (1-2) indicates that the state is not normal.

The processes performed by the signal processing device 100 are not limited to the examples illustrated in FIG. 4.

For example, although FIG. 4 illustrates an example in which the processes in the first function implementation unit 112 ("function 1" illustrated in FIG. 4) of the hardware processing unit 102 are always performed, the processes in the first function implementation unit 112 of the hardware processing unit 102 may be started in a case where the result of determination of the state of the software indicates that the state is not normal ("NG determination" illustrated in FIG. 4).

The signal processing device 100 performs, for example, with the configuration illustrated in FIG. 2, the processes related to the signal processing method according to the present embodiment (e.g., the process (determination process) of the aforementioned (1) and the process (output control process) of the aforementioned (2)).

Therefore, in a case where the software-based image processing on an image signal is normally performed with the configuration illustrated in FIG. 2, for example, the signal processing device 100 can output an image signal on which image processing has been performed by software.

In addition, the signal processing device 100 can exhibit, for example, with the configuration illustrated in FIG. 2, the effect brought about by performing processes related to the signal processing method according to the present embodiment such as, for example, those described above.

Note that the configuration of the signal processing device according to the present embodiment is not limited to the configuration illustrated in FIG. 2.

For example, the signal processing device according to the present embodiment can implement one or both of the determination unit 120 and the output control unit 122 illustrated in FIG. 2 by a processing circuit different from the hardware processing unit 102.

In addition, the signal processing device according to the present embodiment need not include the first function implementation unit 112 "in a case where, for example, image processing on an input image signal is performed in an external image processing hardware having a function similar to the first function implementation unit 112", or "in a case where a configuration is provided in which the second processed image signal is not outputted when the result of determination of the state of the software indicates that the state is not normal".

In addition, for example, the signal processing device according to the present embodiment need not include the output unit 114 in a case where the first processed image signal is selectively outputted in an output device having a function similar to the output unit 114. In the aforementioned case, the signal processing device according to the present embodiment controls the output of the output image signal in the output device by transmitting a control signal to the aforementioned output device, for example.

In addition, in a case where the image processing on an input image signal is performed by software in an external device having a function similar to the software processing unit 104, for example, the signal processing device according to the present embodiment need not include the software processing unit 104. In the aforementioned case, the signal processing device according to the present embodiment determines the state of associated software to be executed in the aforementioned external device, for example.

In addition, as has been described above, the process (determination process) of the aforementioned (1) and the process (output control process) of the aforementioned (2) are processes obtained by dividing the process related to the signal processing method according to the present embodiment for convenience. Therefore, the configuration for implementing the process related to the signal processing method according to the present embodiment is not limited to the determination unit 120 and the output control unit 122 illustrated in FIG. 2 and may have a configuration in accordance with the way of dividing the process related to the signal processing method according to the present embodiment.

Although the present embodiment has been described above taking a signal processing device as an example, the present embodiment is not limited to such a configuration. The present embodiment can be applied to various devices capable of performing the processes related to the signal processing method according to the present embodiment such as, for example, "various medical devices such as an endoscope, CT, MRI, PET, or ultrasonic diagnostic device", "imaging devices such as a broadcast station camera, a digital video camera, or a digital still camera" "communication devices such as a cellular phone or a smart phone", a tablet-type device, "computers such as a personal computer (PC), or a server," a display device, a video/music playback device (or a video/music recording and playback device), a gaming machine, or the like. In addition, the present embodiment can also be applied to a processing integrated circuit (IC) which can be built in the aforementioned devices, for example.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

In addition, the effects described in the present specification are merely illustrative and demonstrative, and not limitative. In other words, the technology according to the present disclosure can exhibit other effects that are evident to those skilled in the art along with or instead of the effects based on the present specification.

Additionally, the present technology may also be configured as below.

(1)

A signal processing device including:

a determination unit configured to determine a state of software associated with image processing on an input image signal indicating an image captured by a medical apparatus; and an output control unit configured to have a first processed image signal that is the input image signal on which image processing has been performed by the software selectively outputted, on the basis of a result of determination of the state of the software.

(2)

The signal processing device according to (1), wherein the determination unit causes hardware executing the software to perform a predetermined process, and determines the state of the software on the basis of a result of the predetermined process.

(3)

The signal processing device according to (2), wherein, in a case where the hardware has a plurality of processor cores, the determination unit causes a part of the plurality of processor cores to perform the predetermined process, and determines the state of the software on the basis of a result of the predetermined process in a part of the processor cores.

(4)

The signal processing device according to (2) or (3), wherein the determination unit determines that the state of the software is not a normal state when, in a case where the predetermined process is a calculation process, the result of the calculation process is erroneous, or when the result of the predetermined process is not available, and the output control unit does not have the first processed image signal outputted when the result of determination of the state of the software is not a normal state.

(5)

The signal processing device according to any one of (1) to (4), wherein the determination unit authenticates the software and determines the state of the software on the basis of an authentication result.

(6)

The signal processing device according to (5), wherein the determination unit determines that the state of the software is not a normal state when the authentication has not been normally completed, and the output control unit does not have the first processed image signal outputted when the result of determination of the state of the software is not a normal state.

(7)

The signal processing device according to any one of (1) to (6), wherein the determination unit determines validity of the first processed image signal on the basis of pixel values included in the first processed image signal, and determines the state of the software on the basis of a result of determination of the validity.

(8)

The signal processing device according to (7), wherein the determination unit determines that the state of the software is not a normal state when the first processed image signal is not determined to be valid, and the output control unit does not have the first processed image signal outputted when the result of determination of the state of the software is not a normal state.

(9)

The signal processing device according to any one of (1) to (8), further including a first image processing unit configured to perform image processing on the input image signal by executing the software, wherein the output control unit has the input image signal that has been image-processed in the first image processing unit selectively outputted as the first processed image signal.

(10)

The signal processing device according to any one of (1) to (9), wherein the output control unit, when not having the first processed image signal outputted, has a second processed image signal that is the input image signal on which image processing has been performed by image processing hardware outputted.

(11)

The signal processing device according to any one of (1) to (10), further including an output unit configured to selectively output the first processed image signal on the basis of a control signal transmitted from the output control unit.

(12)

The signal processing device according to any one of (1) to (11), wherein the image indicated by the input image signal is an endoscope image captured by an imaging device included in an endoscope.

(13)

The signal processing device according to (12), wherein the determination unit determines validity of the first processed image signal on the basis of a predetermined characteristic indicated by the endoscope image, and determines the state of the software on the basis of a result of determination of the validity.

(14)

A signal processing device including:

a software processing unit configured to execute software associated with image processing on an input image signal that has been input; and a hardware processing unit having image processing hardware that performs image processing on the input image signal, wherein the hardware processing unit includes a determination unit configured to determine a state of the associated software, and an output control unit configured to have a first processed image signal that is the input image signal on which image processing has been performed by the executed software selectively outputted, on the basis of a result of determination of the state of the software.

(15)

The signal processing device according to (14), wherein the output control unit, when not having the first processed image signal outputted, has a second processed image signal that is the input image signal on which image processing has been performed by the image processing hardware outputted.

(16)

The signal processing device according to (14) or (15), wherein the determination unit causes hardware executing the software to perform a predetermined process, and determines the state of the software on the basis of a result of the predetermined process.

(17)

The signal processing device according to any one of (14) to (16), wherein the output control unit causes the image processing hardware to perform image processing on the input image signal when the state of the software is determined not to be normal.

(18)

A signal processing method including:

a step of determining a state of software associated with image processing on an input image signal that has been input; and a step of having a first processed image signal that is the input image signal on which image processing has been performed by the software selectively outputted, on the basis of a result of determination of the state of the software.

REFERENCE SIGNS LIST 100 signal processing device
102 hardware processing unit
104 software processing unit
110 monitoring unit
112 first function implementation unit
114 output unit
116 second function implementation unit
120 determination unit
122 output control unit

The invention claimed is:

1. A medical signal processing system, comprising:
logic circuitry configured to:
obtain a medical image signal generated by a medical imaging device;
generate a first medical image based on a first image processing of the medical image signal;
transmit a response request to a graphic processor, wherein
the response request is for a response from the graphic processor within a specific time period, and
the graphic processor generates a second medical image based on a second image processing of the medical image signal;
determine a difference between an amount of characteristic of the first medical image and an amount of characteristic of the second medical image is equal to or greater than a threshold value;
monitor a status of the graphic processor based on one of a presence or an absence of the response from the graphic processor within the specific time period and the determination that the difference is equal to or greater than the threshold value; and
output, in a case that the status of the graphic processor is erroneous, the first medical image.

2. The medical signal processing system according to claim 1, wherein the logic circuitry is a FPGA (Field-Programmable Gate Array).

3. The medical signal processing system according to claim 2, wherein the graphic processor includes a plurality of GPUs.

4. The medical signal processing system according to claim 3, wherein the FPGA is connected to the plurality of GPUs directly.

5. The medical signal processing system according to claim 1, wherein the first image processing requires less computation than the second image processing.

6. The medical signal processing system according to claim 5, wherein the first image processing and the second image processing include a development processing.

7. The medical signal processing system according to claim 6, wherein the second image processing includes an additional processing including at least one of a noise suppressing process, a color correction process, or a high-frequency emphasis process.

8. The medical signal processing system according to claim 7, wherein the first image processing excludes the additional processing.

9. The medical signal processing system according to claim 8, wherein the logic circuitry is further configured to:
   transmit a request for a calculation processing to the graphic processor; and
   determine whether the status of the graphic processor is erroneous based on a result of the calculation processing.

10. The medical signal processing system according to claim 9, wherein the calculation processing includes at least one of an integer calculation processing, an encryption processing, or an authentication processing.

11. The medical signal processing system according to claim 10, wherein
   the medical imaging device is an endoscope imager; and
   the logic circuitry is coupled to the endoscope imager via an interface.

12. The medical signal processing system according to claim 11, wherein the medical image signal is a raw endoscope image signal generated by the endoscope imager.

13. The medical signal processing system according to claim 9, wherein the logic circuitry is further configured to:
   compare the result of the calculation processing with the threshold value, wherein the threshold value is stored in a memory; and
   determine whether the status of the graphic processor is erroneous based on the comparison.

14. A medical imaging processing device, comprising:
logic circuitry configured to:
   obtain a medical image signal generated by a medical imaging device;
   generate a first medical image based on a first image processing of the medical image signal;
   transmit a response request to a graphic processor, wherein
      the response request is for a response from the graphic processor within a specific time period, and
      the graphic processor generates a second medical image based on a second image processing of the medical image signal;
   determine a difference between an amount of characteristic of the first medical image and an amount of characteristic of the second medical image is equal to or greater than a threshold value;
   monitor a status of the graphic processor based on one of a presence or an absence of the response from the graphic processor within the specific time period and the determination that the difference is equal to or greater than the threshold value; and
   output, in a case that the status of the graphic processor is erroneous, the first medical image.

15. A medical imaging processing method, comprising:
obtaining, by logic circuitry, a medical image signal generated by a medical imaging device;
generating, by the logic circuitry, a first medical image based on a first image processing of the medical image signal;
transmitting, by the logic circuitry, a response request to a graphic processor, wherein
   the response request is for a response from the graphic processor within a specific time period, and
   the graphic processor generates a second medical image based on a second image processing of the medical image signal;
determining, by the logic circuitry, a difference between an amount of characteristic of the first medical image and an amount of characteristic of the second medical image is equal to or greater than a threshold value;
monitoring, by the logic circuitry, a status of the graphic processor based on one of a presence or an absence of the response from the graphic processor within the specific time period and the determination that the difference is equal to or greater than the threshold value; and
outputting, by the logic circuitry, the first medical image in a case that the status of the graphic processor is erroneous.

* * * * *